US005154702A

United States Patent [19]

Foyil

[11] Patent Number: 5,154,702

[45] Date of Patent: Oct. 13, 1992

[54] VARIABLE DOSAGE DROPPER SYSTEM

[75] Inventor: Mark L. Foyil, Millville, N.J.

[73] Assignee: Wheaton Industries, Millville, N.J.

[21] Appl. No.: 526,172

[22] Filed: May 21, 1990

[51] Int. Cl.[5] .................... A61M 5/178

[52] U.S. Cl. .................... 604/212; 604/217; 604/298; 215/214; 215/219; 222/43; 222/214; 222/287; 222/309; 222/420

[58] Field of Search .................... 604/207, 208, 212, 217, 604/295, 298; 73/864.11; 222/41, 43, 153, 206, 214, 282, 287, 309, 420, 421; 141/24; 215/201, 204, 214, 215, 217, 219

[56] References Cited

U.S. PATENT DOCUMENTS

| | | | |
|---|---|---|---|
| 519,014 | 5/1894 | Beck | 604/217 |
| 694,530 | 3/1902 | Comer | 222/158 |
| 1,900,201 | 3/1933 | Sager | 604/296 |
| 2,595,493 | 5/1952 | Slaby et al. | 222/214 |
| 2,966,284 | 12/1960 | Lewis | 604/207 |
| 3,101,751 | 8/1963 | Ballin | 141/24 |
| 3,812,990 | 5/1974 | Willis | 215/219 |
| 3,820,576 | 6/1974 | Torrent | 141/24 |
| 4,047,438 | 9/1977 | Sekine | 73/423 A |
| 4,158,035 | 6/1979 | Haase et al. | 422/100 |
| 4,511,534 | 4/1985 | Bennett, Jr. et al. | 422/100 |
| 4,623,337 | 11/1986 | Maurice | 604/298 |

*Primary Examiner*—Randy C. Shay
*Attorney, Agent, or Firm*—Ratner & Prestia

[57] ABSTRACT

A variable dosage dropper system improves upon the conventional dropper assembly (container, cap, pipette, bulb) by providing an annular overcap housing which completely encloses the cap and bulb to provide tamper resistant protection and has a locking collar at its lower end to secure the cap within the housing. A plunger slidably, rotatably, and sealingly mates with the housing. The plunger contacts and compresses the bulb when pushed downward toward the housing a predetermined distance corresponding to various dosages and allows the bulb to return to its decompressed position when released. The system is also adapted to resist undesired opening of the container by children.

35 Claims, 5 Drawing Sheets

VARIABLE DOSAGE DROPPER SYSTEM

BACKGROUND OF INVENTION

A. Field of Invention

The present invention relates, in general, to a measuring device for repetitive and reproducible dispensing of quantitatively predetermined dosages of a liquid such as a medicine held in a container. More specifically, this invention relates to a tamper-resistant, child-resistant, plunger-type dropper assembly which allows variable dosage selectability without using springs or screw threads for plunger return.

B. Description of Related Art

Conventional containers are used to store and transport certain liquids, such as medicines, vitamins, and the like, which often have to be dispensed in small but precise quantities or dosages. Such dosages may be on the order of one milliliter or less and are characteristically dispensed using a pipette and compressible, resilient bulb dropper assembly.

It is often very difficult to draw the exact amounts of liquid in the minute quantities necessary using a conventional dropper assembly. Control of the assembly is especially difficult for relatively unskilled persons, such as consumers. This problem is particularly severe for elderly patients who are generally beset with ailments requiring medication. A brief explanation of the pipetting concept illustrates why such control is difficult.

The pipette, open at both ends, is placed at one end into the substantially air tight liquid container. The compressible bulb is mounted on top of the opposite end of the pipette. Such droppers are often incorporated into the cap or closure used to seal the container and retain the liquid. The pipette is affixed to the cap, usually mounted in the center of the cap in a sealed relationship. One end of the pipette depends into the container when the cap is screwed onto the container and the opposite end of the pipette extends above the cap into the bulb.

Whether a free dropper or a cap-mounted dropper is used, the pipette is first filled with liquid by compressing the bulb with the pipette immersed in the liquid. The bulb may be compressed mechanically with a plunger or by hand. This compression causes the air inside the bulb to expel from the bulb into the container. When the pressure exerted by the plunger or user on the bulb is released, the elasticity of the bulb allows it to return to its initial volume, creating a vacuum in the bulb. That vacuum allows liquid in the container to rise into the pipette. The assembly may then be unscrewed from the container and the liquid contained in the pipette dispensed by exerting anew pressure on the bulb.

Thus, the degree of vacuum created in the bulb is directly related to the amount of liquid drawn into the pipette and subsequently dispensed. It is very difficult to control the vacuum created, and therefore the dosage dispensed. This is true even though the pipette is usually graduated with markings indicating dosage amounts, because it is impossible to expect a smooth dispensing operation. The control problem is especially acute when the dropper is used in the dark or dimly illuminated rooms in which patients often reside.

With the above discussion in mind, it is one object of the present invention to provide a dropper system which allows the user to preselect a precise dosage and to deliver that precise dosage invariably and exactly.

There are devices available which allow the user to fix the depression distance of the bulb and, consequently, to preselect the volume of liquid drawn into the pipette. Few of these devices allow the user, however, to vary the preselected dosage. The ability to provide a variable dosage selectability feature is another object of the invention.

The few devices which do allow variable dosage selectability often require the user to replace one cap with another or one plunger with another of different length in order to achieve a fixed dosage. This requirement wastes user time and increases the cost of the device. Other devices require complex springs, screw threads, or camming mechanics. These requirements cause the devices to become complicated in construction and accordingly expensive.

Therefore, it is a further object of the present invention to provide a dropper system which allows the user to vary the precise dosage preselected without requiring replacement components or incorporating complex mechanics. A related object is to construct the system in a commensurately simple and economic fashion. Still another related object is to construct the system to incorporate a compact outer shape without projecting parts.

When a system allows the user to vary the preselected dosage, an inherent risk arises that the dosage selected may be inadvertently altered. For example, the extent of plunger travel and consequent compression of the bulb may be affected if the cap is mistakenly twisted. Accordingly, related objects of the invention are to (1) fix the preselected dosage once it is set by preventing inadvertent alteration, and (2) provide notice if the system is altered such that the dosage which will be dispensed has changed from that previously selected.

Although the use of a plunger-type pipette and bulb dropper assembly, which applies capillary flow concepts, is sound, the devices previously developed to incorporate plunger activation of the bulb have a common drawback: they do not assure that the plunger will contact the bulb at the center of the bulb. Unless the plunger contacts very nearly the center of the bulb, the bulb may topple over rather than compress symmetrically. Absent a consistent, symmetrical, accordion-like compression of the bulb, the system cannot provide a maximum, hence consistent, draw of liquid upon each use. Thus, still another object of the invention is to assure that the plunger contacts the center of the bulb.

Unfortunately, safety has recently, of necessity, become a high priority in the provision of consumer products including medicines, vitamins, and the like. Accordingly, another object of the invention is to provide a tamper resistant dropper system. Protection even against potential syringe-type injections in the dispensing bulb is within the scope of this object.

In order to further preclude tampering and to protect against even innocent damage to or loss of both the plunger and bulb, it is desirable to enclose these components within a protective housing. Still another object of the present invention is to provide a protective housing which permanently encloses the bulb and prevents complete removal of the plunger from the housing.

An object ancillary to the safety aspect of the two previous objects is to provide a child-resistant system, protecting against undesired opening of the container by small children who may be harmed by the liquid contents. A problem with many caps designed to make a container "child-proof" is the difficulty many adults have in opening them. Many designs require the user to squeeze the cap while twisting it. The force necessary to squeeze the rigid cap is difficult to apply for some users. Some adults afflicted, for example, with arthritis have trouble squeezing caps because their fingers or wrists may be sore. Still another object of this invention is to provide a child-resistant system which does not require a squeezing action for either opening or closing the container.

Finally, it is an object of the present invention to provide a system which uses standard dropper components: pipette, cap, and bulb. By achieving this object, the invention can be manufactured as a complete unit which incorporates such standard components into the system; the invention can also be manufactured for use with preexisting standard dropper systems.

SUMMARY OF THE INVENTION

To achieve these and other objects, and in view of its purposes, the present invention provides a dropper system for providing a variable and consistent liquid dosage. The system incorporates certain standard components. Thus, the system includes a container for holding the liquid and a vertically disposed pipette open at both ends for drawing the liquid from the container and dispensing the liquid. A striated cap is affixed to, and circumferentially encloses, a portion of the pipette and fits over the container to seal the container and retain the liquid inside the container. A bulb is hermetically affixed to the upper end of the pipette for drawing liquid into the pipette upon decompression after compression and releasing the liquid when the bulb is returned to its compressed position.

The system improves upon the conventional dropper assembly by providing an annular overcap housing which surrounds the cap and bulb to provide tamper resistant protection and has a locking collar at its lower end to secure the cap within the housing. A plunger slidably, rotatably, and sealingly mates with the housing. The plunger contacts and compresses the bulb when pushed downward toward the housing a predetermined distance corresponding to various dosages and allows the bulb to return to its decompressed position when pushed upward away from the housing. Finally, the system is adapted to resist undesired opening of the container by children.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawings, in which.

DETAILED DESCRIPTION OF THE INVENTION

Figure 1:
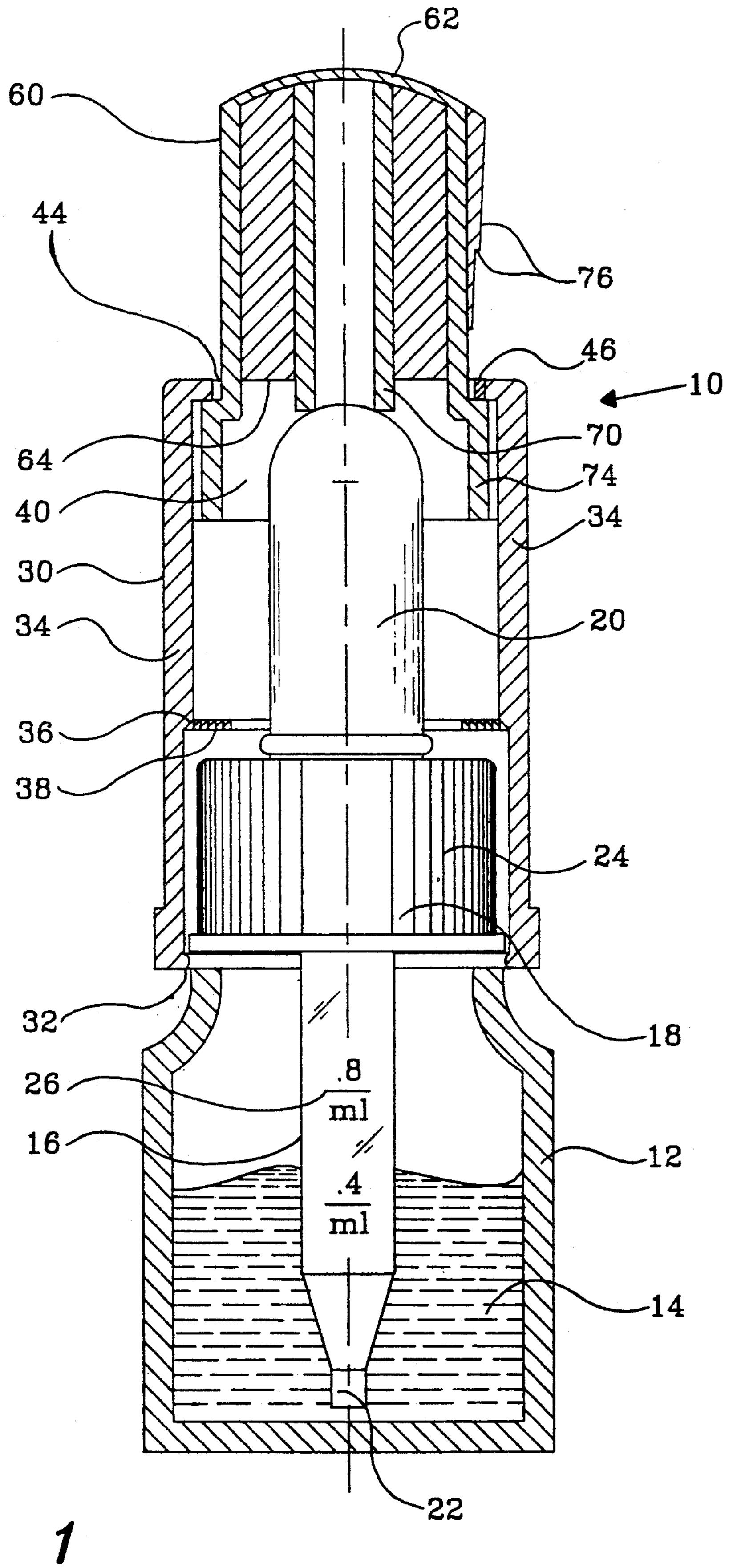
FIG. 1 illustrates a cross-section of the system according to the present invention in an upright, vertical position and shows the system in its "normal" position with the bulb decompressed.

Shown in FIG. 1 is a variable dosage dropper system 10 constructed according to the present invention. System 10 incorporates the standard components of a dropper system: a container 12 for holding liquid 14 such as medicine, vitamins, and the like; a pipette 16; a cap 18; and a bulb 20. System 10 combines with these standard components the additional components of an annular overcap housing 30 and a plunger 60.

Pipette 16 is shown vertically disposed in container 12 with the lower end 22 of pipette 16 immersed in liquid 14. Open at both ends, pipette 16 is able to draw liquid 14 from container 12 and to dispense a variable and consistent dosage of liquid 14. Hermetically affixed to the upper end of pipette 16 is a flexible bulb 20. Cap 18 circumferentially encloses a portion of pipette 16 and is affixed to pipette 16 at a position along the axis of pipette 16 which is below bulb 20 and which allows pipette 16 to extend sufficiently far into container 12 to draw substantially all of liquid 14 from container 12.

Cap 18 fits over container 12 to seal container 12 and to retain liquid 14 within container 12. Cap 18 has striations 24 to facilitate rotation of cap 18, which tracks threads on container 12 and is removed from container 12 when rotated in one direction and placed on container 12 when rotated in the opposite direction. Suitable materials for cap 18 include plastic, metal, and the like.

Graduated markings 26 on pipette 16 allow the user to identify the amount of liquid 14 drawn into pipette 16. To enable identification, pipette 16 is made from a substantially clear material which allows the user to view the level of liquid 14. Suitable materials include glass, plastic, and the like.

Bulb 20 is resilient and elastic, allowing repeated compression and decompression. Suitable materials for construction of bulb 20 include rubber, thermoplastic elastomers, and the like. The standard, cylindrical-type bulb is shown in the Figures and can be incorporated into system 10. A bellows-type bulb, which allows pipette 16 to draw a higher volume of liquid 14 than does the cylindrical type, can also be used. Thus, system 10 can incorporate a variety of different types of bulb 20.

Figure 2A:
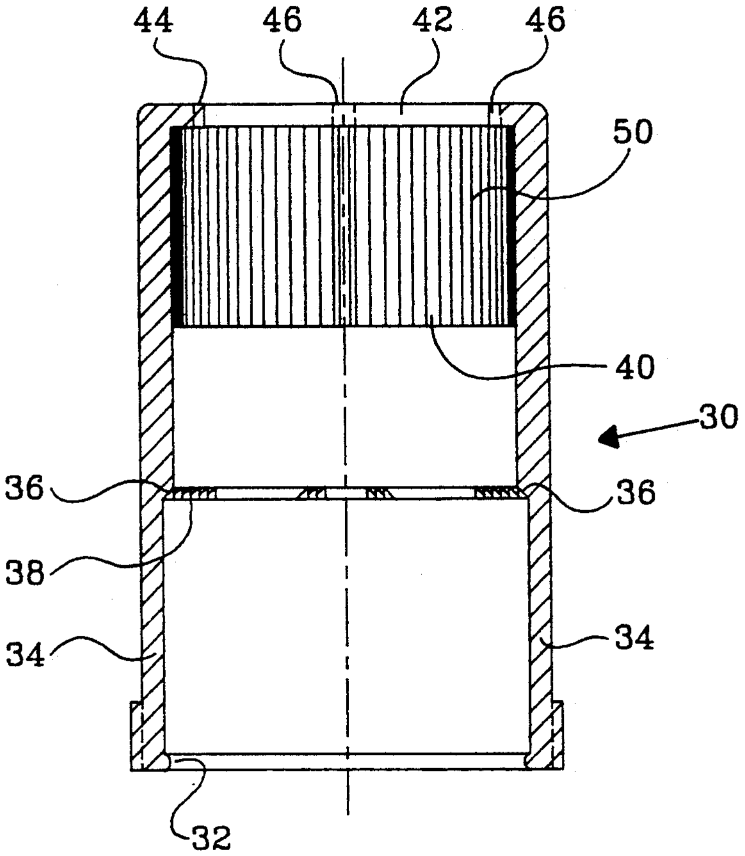
FIG. 2*a* is a cross-section of the housing constructed in accordance with the present invention, shown in the upright, vertical position.
Figure 2B:
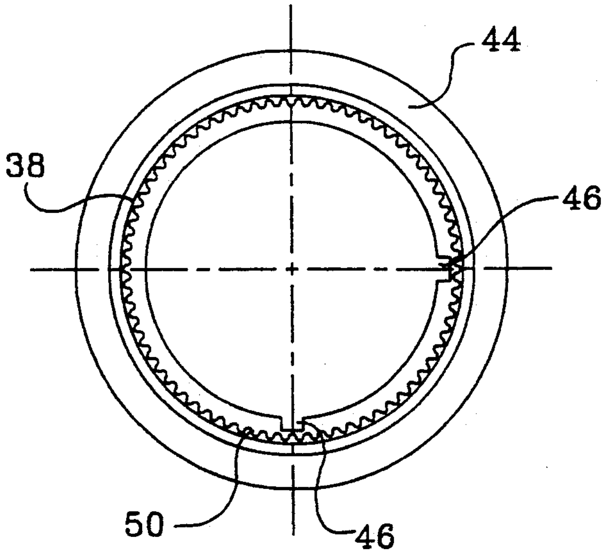
FIG. 2*b* is a bottom view of the housing shown in FIG. 2*a*.

An annular overcap housing 30, made from a rigid material such as plastic, surrounds cap 18 and bulb 20. Shown more explicitly in FIGS. 2*a* and 2*b*, housing 30 has a locking collar 32 at its lower end to secure cap 18 within housing 30. (Note that locking collar 32 is not permanently fixed to cap 18; rather, collar 32 may slide downward below cap 18 along the outside of container 12 and a curved surface may be provided in the top of container 12 to facilitate such travel.) Housing 30 therefore serves a safety function, providing system 10 with tamper resistant protection. The combination of a plunger 60, housing 30, locking collar 32, and container 12 completely encloses cap 18 and bulb 20. Because bulb 20 is encapsulated, the scope of protection extends to cover even potential syringe-type injections in bulb 20.

Housing 30 provides an additional safety feature: child resistance. One way to provide child resistance is shown in FIG. 1. Housing 30 can be pushed axially downward, so that housing walls 34 travel downward relative to cap 18. Travel will continue until the top of cap 18 contacts a circumferential indentation 36 on the inside surface of wall 34. When travel of housing 30 relative to cap 18 is interrupted by indentation 36, cap 18 will be surrounded by a ciroumferential band of ridges 38 located on the inside surface of wall 34. Ridges 38 engage striations 24 of cap 18 and, upon rotation of housing 30, ridges 38 drive striations 18 and turn cap 18. Thus, the combined motions of pushing downward and rotating housing 30 will open or close cap 18. No forceful squeezing action, often difficult for even many adults to achieve, is necessary. Nevertheless, the combined motions are beyond the capabilities of most young children and system 10 resists undesired opening of container 12 by such children.

Figure 3B:
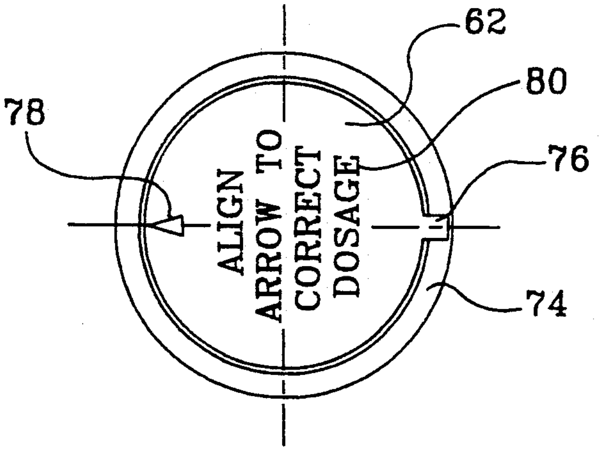
FIG. 3*b* is a top view of the plunger shown in FIG. 3*a*.
Figure 3A:
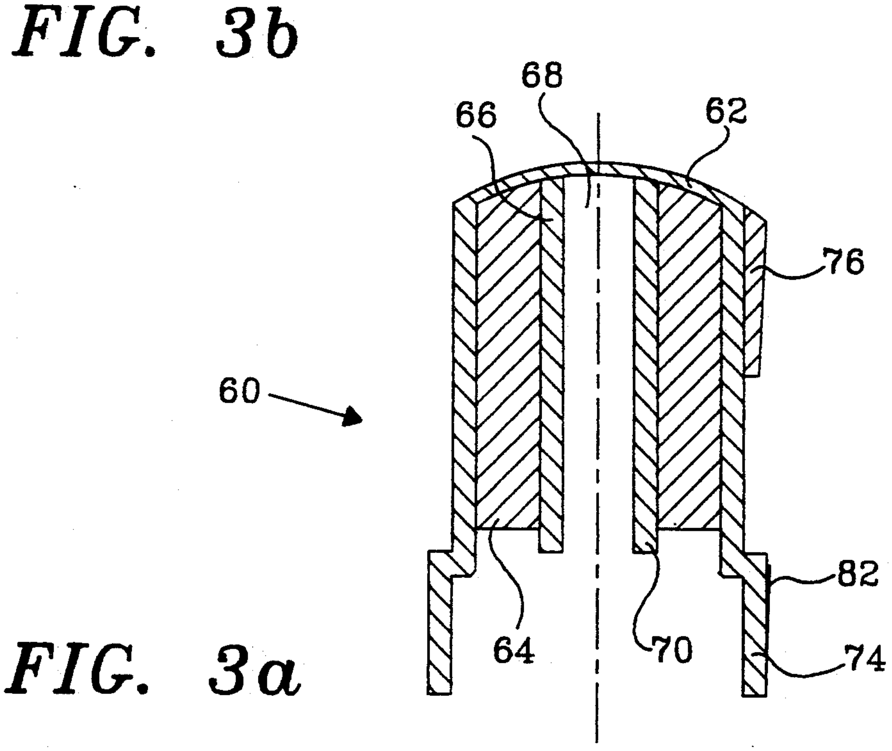
FIG. 3*a* is a cross-section of the plunger constructed in accordance with the present invention, shown in the upright, vertical position.

Plunger 60 slidably, rotatably, and sealingly mates with housing 30. Shown more explicitly in FIGS. 3*a* and 3*b*, plunger 60 is rigid and may be made of plastic. In operation, the user pushes down on the top 62 of plunger 60. As plunger 60 travels downward toward housing 30 and bulb 20, bulb 20 is compressed. Compression expels the air inside bulb 20. When the user releases the pushing force exerted on plunger 60, the elasticity of bulb 20 allows it to return to its initial, decompressed volume-thereby pushing plunger 60 upward away from housing 30 and creating a vacuum inside bulb 20. That vacuum causes liquid 14 to rise into pipette 16. The extent to which bulb 20 is compressed dictates the extent of the vacuum created and, therefore, the amount of liquid 14 drawn into pipette 16. Thus, it is possible to fix the amount of liquid 14 drawn by predetermining the distance of travel by plunger 60 relative to housing 30 and bulb 20.

Figure 4B:
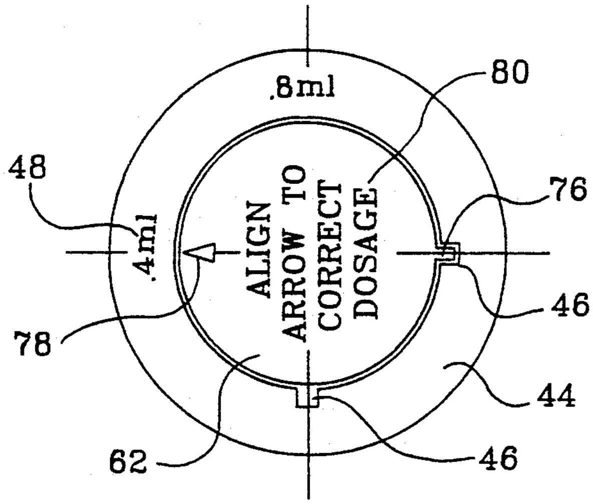
FIG. 4*b* is a top view of the plunger shown in FIG. 4*a*.
Figure 4A:
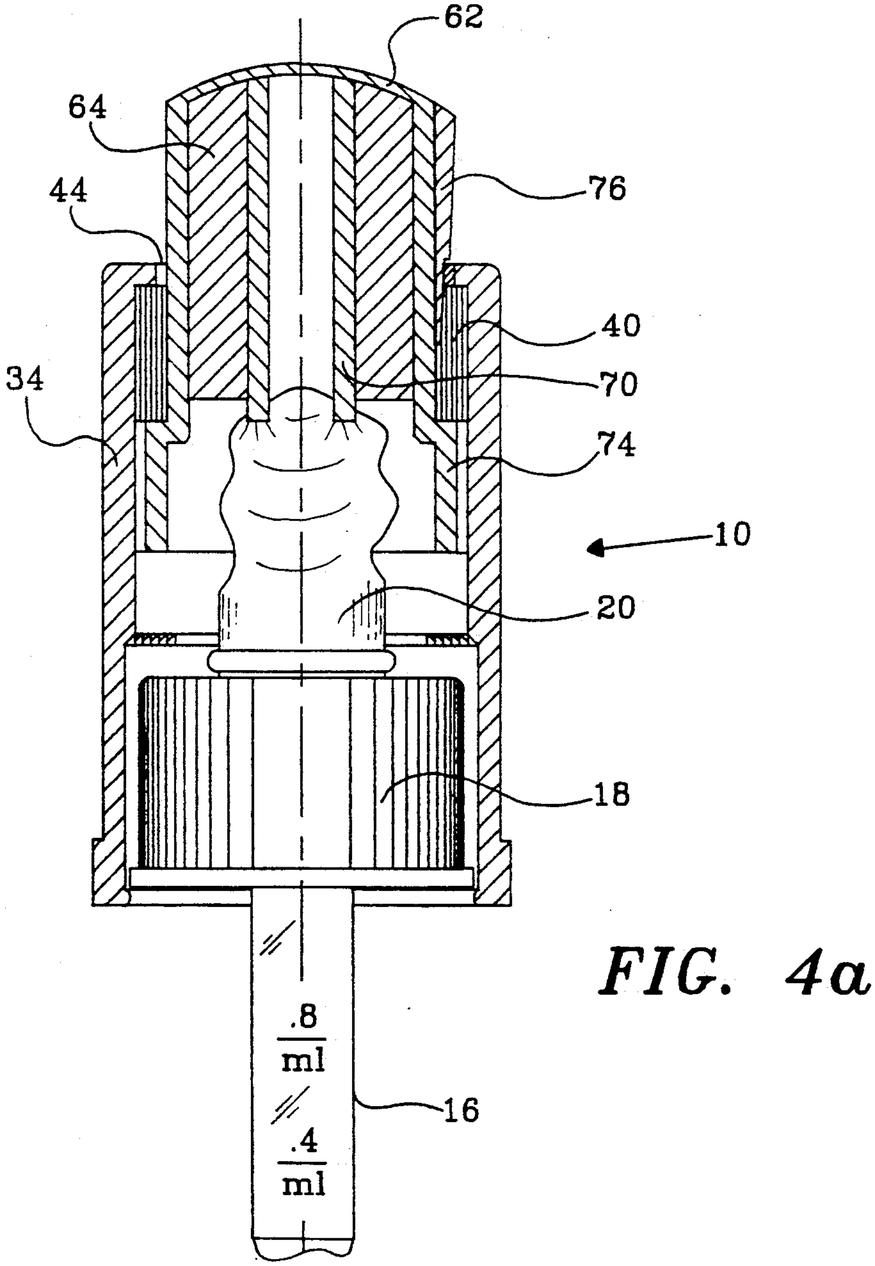
FIG. 4*a* illustrates a cross-section of the system according to the present invention in an upright, vertical position and shows the system with the bulb compressed sufficiently to provide a dosage of, as an example, 0.4 milliliters.
Figure 5B:
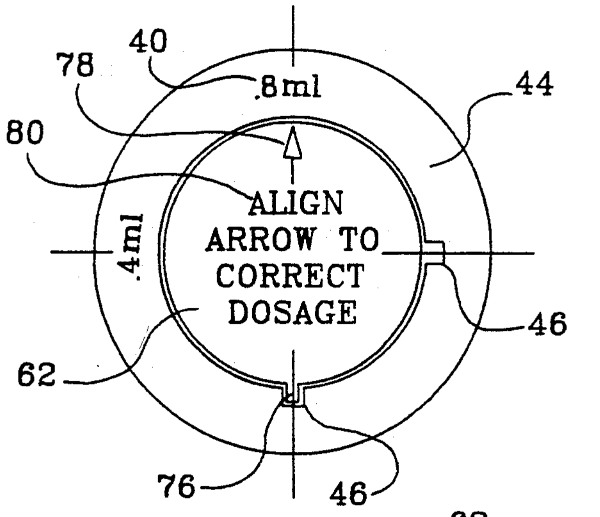
FIG. 5*b* is a top view of the plunger shown in FIG. 5*a*.
Figure 5A:
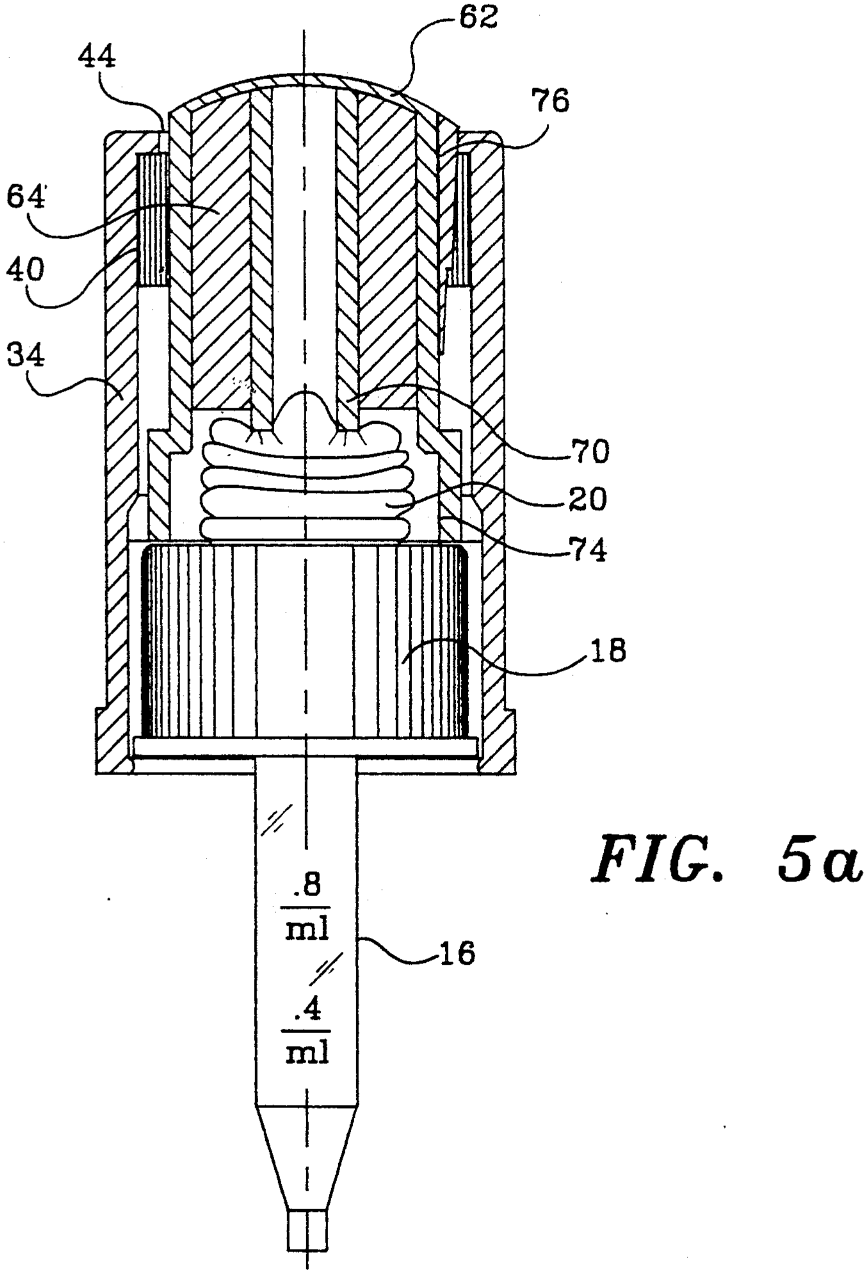
FIG. 5*a* illustrates a cross-section of the system according to the present invention in an upright, vertical position and shows the system with the bulb compressed sufficiently to provide a dosage of, as an example, 0.8 milliliters.

In order to control the vacuum created and to assure repeatability through a maximum draw of liquid 14, plunger 60 must be centered on bulb 20 so that bulb 20 is compressed symmetrically and achieves an accordion-like shape (see FIGS. 4*a* and 5*a*). Unless plunger 60 contacts very nearly the center of bulb 20, bulb 20 may topple over rather than compress symmetrically. System 10 is designed to assure that plunger 60 contacts the center of bulb 20.

Housing 30 is provided with alignment splines 40 (see FIG. 2*a*) positioned circumferentially around the inside surface of wall 34. Splines 40 mate with plunger 60 to restrict horizontal movement of plunger 60 as it travels axially relative to housing 30. Thus, splines 40 help to keep plunger 60 centered over bulb 20. Moreover, when system 10 is in its normal, at rest, position, plunger 60 just contacts the top of bulb 20 (see FIG. 1). Such positioning also assures alignment of plunger 60 on the center of bulb 20.

Design of the structure of plunger 60 which actually contacts bulb 20 allows a number of alternatives. The relative ability of each alternative to satisfy the required function that plunger 60 contact the center of bulb 20 serves to distinguish the alternatives. Accordingly, for the preferred embodiment shown in FIGS. 1, 3*a*, and 3*c*, a plurality of fins 64 extend from the inside surface of plunger 60 toward the center of plunger 60. Fins 64 terminate at and support a ring 66 which forms an axial, central opening 68 in plunger 60. The bottom of ring 66 forms a projecting tip 70 which extends below the bottom of fins 64 and just contacts the top of bulb 20 when bulb 20 is decompressed.

Figure 3C:
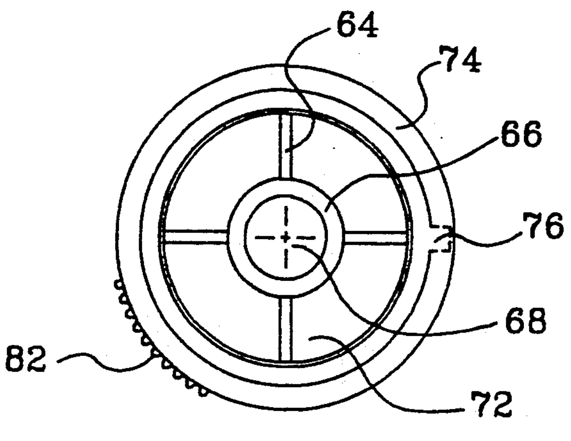
FIG. 3*c* is a bottom view of the plunger shown in FIG. 3*a*.

This preferred embodiment assures that ring 66 contacts bulb 20 before the flat bottoms of fins 64 do. Therefore, ring 66 can position bulb 20 properly for subsequent contact by fins 64 (see FIG. 5*a*), thereby assuring symmetric compression of bulb 20. As shown in FIG. 3*c*, fins 64 can be evenly spaced around the circumference of plunger 60. Four fins 64 are shown as an example, but more or fewer fins are suitable. This embodiment, which includes a central opening 68 and discrete fins 64 separated by hollow spaces 72, offers the added advantage of material savings.

In a second embodiment of the structure by which plunger 60 contacts bulb 20, fins 64 may merge to form a single, solid fin. This embodiment fails to provide the materials savings achieved by the preferred embodiment.

In a third embodiment, whether discrete fins 64 or a single, solid fin is used, the fin or fins may terminate in a single, solid projection tip rather than a tip 70 having a central opening 68. To function properly, however, the tip must contact the center of bulb 20. This contact is difficult to assure with a single tip because the bulb may not return to a precise upright position upon decompression after each use. The ring 66 of the preferred embodiment compensates for this occurrence by allowing bulb 20 to "work" its way into an upright position as ring 66 engages bulb 20. A single tip would not allow for such compensation.

A fourth, and least preferred, embodiment would have a single, solid fin without any projection tip. Thus, the fin would present a flat surface to bulb 20 upon contact. Unless the fin happened to contact bulb 20 very near its center, bulb 20 would be likely to topple over rather than depress symmetrically downward. The desired accordion effect in bulb 20 as it compressed (see FIGS. 4*a* and 5*a*) would not likely be obtained. Nevertheless, despite its drawbacks, such a construction is possible.

As shown in FIG. 1, top 62 of plunger 60 protrudes from hole 42 in housing 30 formed by a horizontally extending rim 44 at the upper end of housing 30. The bottom portion of plunger 60 is always retained, however, within protective housing 30. Such retention serves the tamper-resistant function of system 10 by precluding access to bulb 20.

Although a number of ways to prevent complete removal of plunger 60 from housing 30 can be envisioned, a preferred embodiment is illustrated in FIG. 1. Plunger 60 is provided on its bottom portion with circumferential spline ribs 74. The "Z" shape of ribs 74 allows ribs 74 to contact rim 44 of housing 30 when plunger 60 is pushed or pulled upward. Thus, plunger 60 is retained, at least along part of its length, inside housing 30 and access to bulb 20 through hole 42 is prevented.

It can now be pointed out that system 10 provides child resistance without requiring additional components such as ramps, springs, or the like. When housing 30 is pushed downward so that ridges 38 on wall 34 Of housing 30 engage striations 24 of cap 18, thereby allowing cap 18 to be opened or closed, rim 44 will contact ribs 74 and simultaneously push plunger 60 downward. Thus, bulb 20 will simultaneously be compressed. Once cap 18 is opened or closed, the user will release the downward force on housing 30. The elasticity of bulb 20 will then force plunger 60 upward as bulb 20 resumes its decompressed volume. Ribs 74 of plunger 60 will contact rim 44 and, in turn, force housing 30 to its original position-disengaging ridges 38 from striations 24.

It is desirable to allow the user to preselect a variable and consistent dosage. This desired feature can be achieved by allowing the user to predetermine the downward travel distance of plunger 60, thus defining the compression distance of bulb 20, which, in turn, fixes the volume of liquid 14 (the dosage) drawn into pipette 16. A preferred way to allow the user to predetermine the travel distance of plunger 60 is shown in the Figures.

Rim 44 of housing 30 is provided with one or more alignment notches 46. The number of notches 46 provided corresponds with the number of different dosages which system 10 will allow the user to preselect. If more than one notch 46 is provided, each notch will have a different width.

A stepped stop lug 76 is attached to the top of the outside wall of plunger 60. Lug 76 cooperatively engages notches 46 of housing rim 44 and will have as many steps as there are notches 46. Thus, in FIGS. 3*a*, 3*b*, and 3*c* one notch 46 and a one-stepped lug 76 are shown, and system 10 can deliver a single preselected dosage. In FIGS. 2*a*, 2*b*, 4*a*, 4*b*, 5*a*, and 5*b*, two notches 46 and a two-stepped lug 76 are shown and system 10 can deliver two preselected dosages-for example, dosages of 0.4 and 0.8 ml. Clearly, additional preselected dosages would be possible given additional notches 46 and steps on lugs 76.

When system 10 is in its normal, at rest, position, plunger 60 just contacts the top of bulb 20 and lug 76 does not engage notches 46 (see FIG. 1). In order to allow the user to align lug 76 with the appropriate notch 46 to select a given dosage, markings 48 (see FIGS. 4*b* and 5*b*) which indicate the various dosage levels possible are positioned on the top surface of rim 44. An indicating arrow 78, and possibly user instructions 80, are positioned on the top 62 of plunger 60. In operation, the user follows instructions so and rotates plunger 60 until arrow 78 corresponds to the correct dosage indicated by marking 48. Such rotation will also align lug 76 with the appropriate notch 46 in housing rim 44 to assure delivery of the desired dosage.

Suppose, for example, that the user desires a dosage of 0.4 ml. The user would rotate plunger 60 until arrow 78 aligns with the 0 4 ml marking 48 (see FIG. 4*b*). That action would also align lug 76 with the thinner (less wide) of the two notches 46. When the user subsequently pushes plunger 60 downward, lug 76 will pass through notch 46 a predetermined distance until the step in lug 76 contacts rim 44. This predetermined distance allows plunger 60 to compress bulb 20 a measured amount sufficient to draw 0.4 ml of liquid 14 into pipette 16 (see FIG. 4*a*).

Now suppose, for example, that the user desires a dosage of 0.8 ml. The user would rotate plunger 60 until arrow 78 aligns with the 0.8 ml marking 48 (see FIG. 5*b*). That action would also align lug 76 with the wider of the two notches 46. When the user subsequently pushes plunger 60 downward, lug 76 will pass completely through notch 46 a predetermined distance until the bottom of plunger 60 contacts cap 18. This predetermined distance allows plunger 60 to compress bulb 20 a measured amount sufficient to draw 0.8 ml of liquid 14 into pipette 16 (see FIG. 5*a*).

In the manner described above, the user is provided with the ability to preselect a dosage and to vary the dosage selected. That ability is provided without requiring the user to replace components of system 10 and without constructing system 10 with complex springs, screw threads, or camming mechanics.

Any assembly which allows the user to vary the preselected dosage risks inadvertent alteration of the dosage selected. Thus, inadvertent rotation of plunger 60 by the user or by another would eliminate the alignment of notch 46 and lug 76 required to provide the dosage selected. It is desirable both to prevent inadvertent alteration of plunger 60 thereby fixing the desired dosage in place once the dosage is set and to provide notice when the plunger is rotated away from the preselected dosage.

System 10 achieves both desired features. As mentioned above, housing 30 has alignment splines 40 (see FIG. 2*a*) positioned circumferentially around the inside surface of wall 34. Splines 40 have serrations 50 which mate with teeth 82 on spline ribs 74 of plunger 60 to provide rotational resistance. Therefore, a certain amount of force is required to rotate plunger 60 against the resistance provided by splines 40 in order to select a dosage. Accordingly, once set, the dosage will remain fixed until a similar force is again asserted to vary the setting. Inadvertent rotation of plunger 60 is avoided.

Splines 40 are also provided with serrations 50 in order to provide notice that plunger 60 is in the process of being rotated away from the previously preselected dosage. As teeth 82 of plunger 60 are rotated against serrations 50 of splines 40, a clickingtype noise occurs which gives the user warning that rotation is occurring.

System 10 according to the present invention can be manufactured as a complete unit which incorporates the standard components—container 12, pipette 16, cap 18, and bulb 20. Alternatively, housing 30, plunger 60, and the components provided along with housing 30 and plunger 60 may be separately manufactured and provided for use with already-existing, standard dropper systems comprising the standard components mentioned above. In that way, the desirable features of system 10, which include tamper resistant protection, child resistant protection, and variable and consistent dosage selectability, could be adapted to existing, conventional dropper assemblies.

Although the invention is illustrated and described herein as embodied in a variable dosage dropper system, which comprises a container, a pipette, a cap, a bulb, a housing, a plunger, and structure assuring childresistance, it is nevertheless not intended to be limited to the details shown. Rather, various modifications may be made in the details within the scope and range of equivalents of the claims and without departing from the spirit of the invention.

What is claimed is:

1. A variable dosage dropper system for providing a liquid dosage which comprises:

a container for holding the liquid;

a vertically disposed pipette open at both ends for drawing the liquid from the container and dispensing the liquid;

a striated cap affixed to and circumferentially enclosing a portion of the pipette the fitting over the container to seal the container and retain the liquid inside the container;

a bulb hermetically affixed to the upper end of the pipette for drawing liquid into the pipette upon decompression following compression and releasing the liquid upon return to the compressed position;

an annular overcap housing surrounding the cap and bulb to provide tamper resistant protection and having a locking collar at its lower end for securing the cap within the housing;

a plunger slidably, rotatably, and sealingly mating with the housing which contacts and compresses the bulb when pushed downward toward the housing a predetermined distance and which allows the bulb to return to its decompressed position when pushed upward away from the housing; and means for centering the plunger on the bulb, said centering means comprising alignment splines positioned circumferentially around the inside wall of the housing for mating with the plunger and restricting horizontal movement of the plunger.

2. A variable dosage dropper system as claimed in claim 1 wherein the pipette is graduated with a series of markings for indicating the amount of liquid present in the pipette.

3. A variable dosage dropper system as claimed in claim 2 wherein the pipette is made from a material allowing the level of liquid to be viewed and is selected from the group consisting of glass and plastic.

4. A variable dosage dropper system as claimed in claim 1 wherein the cap is made from a material selected from the group consisting of plastic and metal.

5. A variable dosage dropper system as claimed in claim 1 wherein the bulb is resilient and is selected from the group consisting of bellows-type bulbs and cylindrically shaped bulbs.

6. A variable dosage dropper system as claimed in claim 5 wherein the bulb is made from a material chosen from the group consisting of rubber and thermoplastic elastomers.

7. A variable dosage dropper system as claimed in claim 1 wherein the housing is made of rigid plastic.

8. A variable dosage dropper system as claimed in claim 1 wherein the plunger is made of rigid plastic.

9. A variable dosage dropper system as claimed in claim 1 further comprising means for resisting undesired opening of the container by children, said child resistant means having a circumferential indentation in the inside wall of the housing for contacting the top of the cap when the housing is pushed downward toward the cap and a circumferential band of ridges on the inside wall of the housing for engaging the striations of the cap when the housing indentation reaches the cap, whereby turning of the housing once engagement between the ridges and striations is achieved will rotate the cap and allow the cap to be removed from and placed on the container.

10. A variable dosage dropper system as claimed in claim 1 wherein the centering means further comprises:

a plurality of fins extending from the inside surface of the plunger to the center of the plunger and terminating at and supporting a ring which forms an axial central opening in the plunger; and a projecting tip formed on the bottom of the ring which extends below the bottom of the fins and just contacts the top of the bulb when the bulb is decompressed to assure alignment of the projecting tip of the ring of the plunger around the center of the bulb.

11. A variable dosage dropper system as claimed in claim 10 wherein the fins are evenly spaced circumferentially around the plunger.

12. A variable dosage dropper system as claimed in claim 1 wherein the top of the plunger protrudes from the top of the housing and the bottom of the plunger is retained within the housing.

13. A variable dosage dropper system as claimed in claim 12 further comprising means for preventing complete removal of the plunger from inside the housing.

14. A variable dosage dropper system as claimed in claim 13 wherein the removal preventing means comprises circumferential spline ribs on the bottom of the plunger which contact the housing when the plunger is moved upward, thereby preventing complete removal of the plunger from within the housing.

15. A variable dosage dropper system as claimed in claim 1 further comprising means for selecting a variable and consistent dosage.

16. A variable dosage dropper system as claimed in claim 15 wherein the selecting means comprises:

(a) a horizontally extending rim at the upper end of the housing containing at least one alignment notch; and (b) a stepped stop lug attached to the top of the outside wall of the plunger for cooperative engagement with the notches in the housing rim, whereby the stop, when aligned with the appropriate notch, allows the plunger to travel a predetermined distance and thereby to compress the bulb a measured amount before the stop contacts the housing rim.

17. A variable dosage dropper system as claimed in claim 16 further comprising means for preventing inadvertent rotation of the plunger thereby fixing the desired dosage in place once the dosage is selected.

18. A variable dosage dropper system as claimed in claim 17 wherein the rotation preventing means comprises alignment splines positioned circumferentially around the inside wall of the housing and teeth located on the bottom portion of the plunger, whereby the splines mate with the teeth to provide rotational resistance and to fix the desired dosage in position.

19. A variable dosage dropper system as claimed in claim 16 further comprising means for providing notice when the plunger is rotated away from the selected dosage.

20. A variable dosage dropper system as claimed in claim 19 wherein the notice providing means comprises serrated alignment splines positioned circumferentially around the inside wall of the housing and teeth located on the bottom portion of the plunger, whereby mating of the splines and teeth creates a clicktype noise providing notice when the plunger is rotated and a new dosage is chosen.

21. A variable dosage dropper system as claimed in claim 16 wherein the selecting means further comprises:

(a) markings on the top surface of the rim of the housing indicating various dosage levels; and (b) an indicating arrow on the top surface of the plunger for aligning the plunger upon rotation with the desired dosage amount marked on the housing rim, thereby aligning the stop lug of the plunger with the appropriate notch in the housing rim to assure delivery of the desired dosage.

22. In a variable dosage dropper system for providing a liquid dosage comprising a container for holding the liquid; a vertically disposed pipette open at both ends for drawing the liquid from the container and dispensing the liquid; a striated cap affixed to and circumferentially enclosing a portion of the pipette and fitting over the container to seal the container and retain the liquid inside the container; and a bulb hermetically affixed to the upper end of the pipette for drawing liquid into the pipette upon decompression following compression and releasing the liquid upon return to the compressed position, the combination with the container, pipette, cap, and bulb of;

(a) an annular overcap housing surrounding the cap and bulb to provide tamper resistant protection and having a locking collar at its lower end for securing the cap within the housing;

(b) a plunger slidably, rotatably, and sealingly mating with the housing which contacts and compresses the bulb when pushed downward toward the housing a predetermined distance and which allows the bulb to return to its decompressed position when pushed upward away from the housing, whereby a variable and consistent liquid dosage is dispensed; and (c) means for centering the plunger on the bulb, said centering means comprising alignment splines positioned circumferentially around the inside wall of the housing for mating with the plunger and restricting horizontal movement of the plunger.

23. A variable dosage dropper system as claimed in claim 22 further comprising means for resisting undesired opening of the container by children, said child resistant means having a circumferential indentation in the inside wall of the housing for contacting the top of the cap when the housing is pushed downward toward the cap and a circumferential band of ridges on the inside wall of the housing for engaging the striations of the cap when the housing indentation reaches the cap, whereby turning of the housing once engagement between the ridges and striations is achieved will rotate the cap and allow the cap to be removed from and placed on the container.

24. A variable dosage dropper system as claimed in claim 22 wherein the centering means further comprises:

a plurality of fins extending from the inside surface of the plunger to the center of the plunger and terminating at and supporting a ring which forms an axial central opening in the plunger; and a projecting tip formed on the bottom of the ring which extends below the bottom of the fins and just contacts the top of the bulb when the bulb is decompressed to assure alignment of the projecting tip of the ring of the plunger around the center of the bulb.

25. A variable dosage dropper system as claimed in claim 24 wherein the fins are evenly spaced circumferentially around the plunger.

26. A variable dosage dropper system as claimed in claim 32 further comprising means for preventing inadvertent rotation of the plunger thereby fixing the desired dosage in place once the dosage is selected.

27. A variable dosage dropper system as claimed in claim 26 wherein the rotation preventing means comprises alignment splines positioned circumferentially around the inside wall of the housing and teeth located on the bottom portion of the plunger, whereby the splines mate with the teeth to provide rotational resistance and to fix the desired dosage in position.

28. A variable dosage dropper system as claimed in claim 22 wherein the top of the plunger protrudes from the top of the housing and the bottom of the plunger is retained within the housing.

29. A variable dosage dropper system as claimed in claim 28 further comprising means for preventing complete removal of the plunger from inside the housing.

30. A variable dosage dropper system as claimed in claim 29 wherein the removal preventing means comprises circumferential spline ribs on the bottom of the plunger which contact the housing when the plunger is moved upward, thereby preventing complete removal of the plunger from within the housing.

31. A variable dosage dropper system as claimed in claim 22 further comprising means for selecting a variable and consistent dosage.

32. A variable dosage dropper system as claimed in claim 31 wherein the selecting means comprises:

(a) a horizontally extending rim at the upper end of the housing containing at least one alignment notch; and (b) a stepped stop lug attached to the top of the outside wall of the plunger for cooperative engagement with the notches in the housing rim, whereby the stop, when aligned with the appropriate notch, allows the plunger to travel a predetermined distance and thereby to compress the bulb a measured amount before the stop contacts the housing rim.

33. A variable dosage dropper system as claimed in claim 32 further comprising means for providing notice when the plunger is rotated away from the selected dosage.

34. A variable dosage dropper system as claimed in claim 33 wherein the notice providing means comprises serrated alignment splines positioned circumferentially around the inside wall of the housing and teeth located on the bottom portion of the plunger, whereby mating of the splines and teeth creates a clicktype noise providing notice when the plunger is rotated and a new dosage is chosen.

35. A variable dosage dropper system as claimed in claim 32 wherein the selecting means further comprises:

(a) markings on the top surface of the rim of the housing indicating various dosage levels; and (b) an indicating arrow on the top surface of the plunger for aligning the plunger upon rotation with the desired dosage amount marked on the housing rim, thereby aligning the stop lug of the plunger with the appropriate notch in the housing rim to assure delivery of the desired dosage.

* * * * *